United States Patent [19]

Buchan

[11] 4,375,667

[45] Mar. 1, 1983

[54] PERSONAL AIR SAMPLING SYSTEM

[76] Inventor: Roy M. Buchan, 304 Flicker Dr., Fort Collins, Colo. 80526

[21] Appl. No.: 220,320

[22] Filed: Dec. 29, 1980

Related U.S. Application Data

[63] Continuation-in-part of Ser. No. 178,136, Aug. 14, 1980, abandoned.

[51] Int. Cl.$^3$ .................. G06F 15/42; G01N 1/22
[52] U.S. Cl. ............................. 364/418; 73/861; 73/863.23; 364/510
[58] Field of Search ............ 364/416, 509, 510, 564, 364/555; 73/195, 198, 227, 861, 861.02, 861.07, 861.35, 861.36, 861.52, 861.59, 861.64, 861.73, 861.85, 863.23, 861.34; 235/92 PC

[56] References Cited

U.S. PATENT DOCUMENTS

| | | | |
|---|---|---|---|
| 3,279,251 | 10/1966 | Chanaud | 73/861.34 |
| 3,965,748 | 6/1976 | Boubel et al. | 73/863.23 |
| 4,080,832 | 3/1978 | Moody et al. | 73/863.23 |
| 4,167,870 | 9/1979 | Haas | 73/861.07 |
| 4,217,777 | 8/1980 | Newman | 73/227 |
| 4,246,788 | 1/1981 | Olin et al. | 73/863.23 |

OTHER PUBLICATIONS

Nutter et al., "Coal Mine Ventilation Remote Control Utilizing a Microprocessor", Industry Appl. Conf.–IEEE–9/30–10/4, 1979, pp. 1184–1190.

Primary Examiner—Errol A. Krass
Attorney, Agent, or Firm—Quarles & Brady

[57] ABSTRACT

A thermal anemometer is employed to detect the velocity of the air flowing through a personal air sampling device. A microprocessor system is employed to periodically read the signal from the thermal anemometer and calculate the sample air flow rate. The measured flow rate is integrated over the sample period to provide an indication of the total volume of air sampled. Flow rates need not be calibrated during the sample period to insure accurate collection data, thus providing an automated and accurate means for measuring air quality.

11 Claims, 6 Drawing Figures

PERSONAL AIR SAMPLING SYSTEM

RELATED APPLICATION

This is a continuation-in-part of application Ser. No. 178,136 filed Aug. 14, 1980 and now abandoned.

BACKGROUND OF THE INVENTION

The field of the invention is personal air sampling devices which can be worn or carried by workers to monitor air quality during a work shift.

Personal air sampling devices are carried by an individual as he performs his normal duties. At the end of a work shift, an air contaminant collection device in the air sampler is removed and inspected to determine the amount of airborne particulate matter or gases to which the individual was exposed. Prior air sampling instruments contain small battery operated air pumps which continuously draw air through the contaminant collection device during the work shift.

The accuracy of prior air sampling devices is dependent on the volume of sampled air delivered by the pump. In early devices a rotameter was calibrated at the beginning and end of a work shift and an average air flow rate was approximated for the entire shift. The volume of sampled air was then calculated using this average air flow rate. Such prior systems were not accurate and, when employed as part of a continuous monitoring program, considerable manpower is required to calibrate the devices and perform the calculations.

More recently, attempts have been made to increase the accuracy of personal air sampling devices. As disclosed in U.S. Pat. No. 4,080,832 for example, a specially designed air pump is used which draws a fixed volume of air through the filter during each stroke. The strokes are counted and employed to calculate the total volume of the air sample during the work shift. In other commercially available devices, the pump is controlled to produce a constant flow rate throughout the sampling time period.

SUMMARY OF THE INVENTION

The present invention is a personal air sampling device in which an air velocity sensor is employed to continuously monitor the air velocity in a passageway containing the contaminant collection device, and means is provided for periodically reading the output of the air velocity sensor and calculating the sample air flow rate. By integrating the measured flow rates over time, the total air volume is calculated and available at the end of the sampling time period.

A general object of the invention is to measure directly the total volume of air sampled during a given time period. The air velocity is directly measured using a thermal anemometer. This measurement is performed repeatedly during the sample period at a rate in excess of the response time of the instrument to changes in velocity. As a result, continuous monitoring of actual velocity is effectively achieved. The velocity numbers are multiplied by the cross sectional area of the passageway to arrive at the volume of air per unit time and these numbers are added to provide a total volume of air flow during the sample time period. Although the measured velocity numbers can be used as a feedback signal to control the operation of the air pump, accuracy is assured by actually calculating the air volume flowing through the filter during the sample time period.

Another object of the invention is to provide an air sampling device which employs microelectronics to enhance the measurement accuracy. A programmed microprocessor is employed to input velocity numbers from the thermal anemometer and to perform the calculations required to provide the up-to-date air volume number. This number as well as other data, including elapsed time, may be read out through a display which is driven by the microprocessor system. The microprocessor may also be coupled to drive the air pump and programmed to maintain a reasonably constant air flow through the filter throughout the sample period.

A more specific object of the invention is to provide a reliable, accurate and relatively low cost means for measuring air flow. A constant power thermal anemometer is employed and its output is linearized by the microprocessor system using a second order interpolation technique. The computing power of the microprocessor thus enables the use of a velocity sensor which is highly accurate at the low rates associated with personal air sampling devices.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

DESCRIPTION OF THE PREFERRED EMBODIMENT

Figure 1:
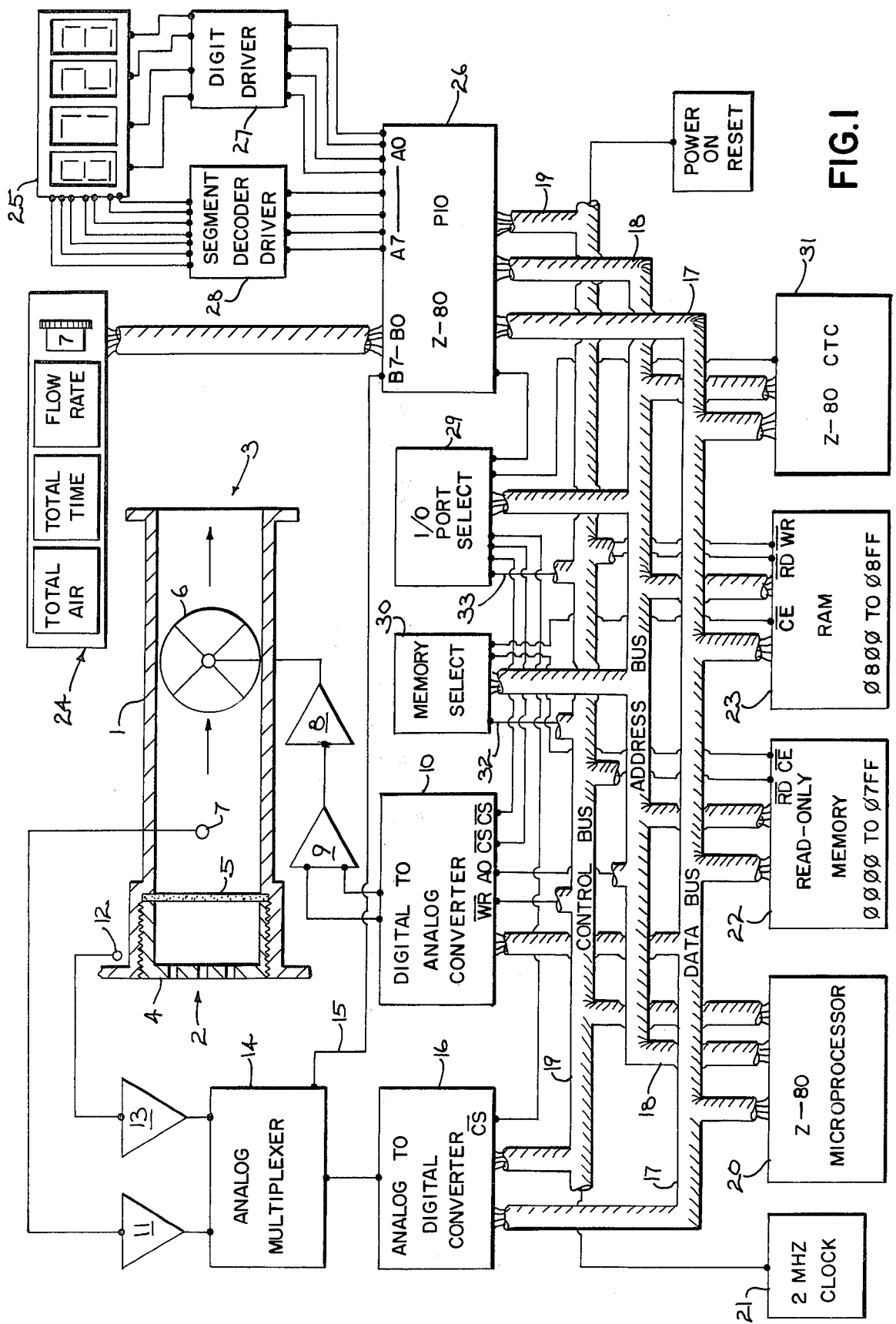
FIG. 1 is a schematic diagram of the personal air sampling system of the present invention.

Referring particularly to FIG. 1, the air sampling system includes a housing 1 which defines a passageway having an air intake 2 and an exhaust opening 3. A cover 4 is received in the housing 1 at the air intake 2 and it entraps a disc-shaped air contaminant collection device 5 in place immediately behind the cover 4. An air pump 6 is disposed in the passageway toward the exhaust 3 and a thermal anemometer 7 is mounted in the passageway behind the collection device 5. The air pump 6 is operated by a small d.c. motor which is controlled by a power amplifier 8 to provide a relatively constant flow of air through the housing 1. The power amplifier 8 is in turn driven by an operational amplifier 9 which receives a speed command signal from a digital to analog converter circuit 10.

The thermal anemometer 7 generates a current to an operational amplifier 11 which has a magnitude that is a function of the air velocity through the passageway. A temperature sensor 12 is mounted to the housing 1 and is connected to a second operational amplifier 13 to provide a current which is proportional to the ambient temperature. The outputs of the operational amplifiers 11 and 13 connect to respective inputs on a two channel analog multiplexer circuit 14. The analog multiplexer 14 is controlled by a select line 15 to input either the anemometer signal or the ambient temperature signal to an analog to digital converter 16 which forms part of a microprocessor system. As will be described in detail below, the microprocessor system operates to periodically read the anemometer signal, correct it to account for the current ambient temperature and linearize it to provide an accurate indication of air velocity in the housing passageway.

The microprocessor system is structured around an 8-bit bi-directional data bus 17, an 8-bit address bus 18 and a control bus 19. These buses connect to an 8-bit microprocessor manfactured by Zilog, Inc. and sold commercially as the model Z-80. The microprocessor 20 is driven by a two megahertz clock 21 and it operates in response to a set of instructions stored in a read-only memory (ROM) 22. The digital to analog converter 10 and the analog to digital converter 16 also connect to the data bus 17 and the microprocessor 20 operates in response to selected instructions to input 8-bit bytes of data from the converter 16 and to output 8-bit bytes of data to the converter 10. This data is stored in a random access memory (RAM) 23 along with other input/output data and along with data which results from calculations performed by the microprocessor 20.

A set of data input switches 24 and a four-digit display 25 are connected to the microprocessor system through a parallel input/output circuit (PIO) 26. The PIO 26 is initialized during power-up such that eight of its terminals A0-A7 are outputs. Terminals B0-B6 are employed as inputs from the switches 24, and B7 is an output to the multiplexer control line 15.

The switches 24 include a 4-bit air flow select switch and three single bit display select switches. The air flow select switch is manually set to one of 10 settings which establish the preset air flow rate in the passageway. The display select switches may be operated to selectively display the actual air flow rate at the moment the switch is closed, the elapsed time since the sample period was begun, and the total air volume which has passed through the collection device 5 during the sample period. The display 25 includes four seven-segment display devices which are enabled by a digit driver circuit 27 and selected by a seven-segment decoder/driver circuit 28.

The elements of the microprocessor system are enabled when selected addresses are generated on the address bus 18. These addresses are decoded by an I/O port select circuit 29 and a memory select circuit 30 to enable the PIO 26, D/A converter 10, A/D converter 16, a Z-80 CTC 31 or the read-only memory 22 or RAM 23. Table A is a list of the hexadecimal addresses of these elements.

TABLE A

| Device | Address | Label |
| --- | --- | --- |
| A/D converter 16 | 0000 | ADCPT |
| D/A converter 10 (bits 0-7) | 0004 | DACPT1 |
| D/A converter 10 (bits 8 & 9) | 0005 | DACPT2 |
| D/A converter 10 (data transfer) | 0008 | DACXFR |
| CTC 31 (#1 timer) | 000C | CTCPT1 |
| CTC 31 (#2 timer) | 000D | CTCPT2 |
| CTC 31 (#3 timer) | 000E | CTCPT3 |
| CTC 31 (#4 timer) | 000F | CTCPT4 |
| PIO 26 (port A data) | 0010 | DSPPT |
| PIO 26 (port A command) | 0011 | DSPCMD |
| PIO 26 (port B data) | 0012 | SWTPT |
| PIO 26 (port B command) | 0013 | SWTCMD |
| ROM 22 | 0000-07FF | |

TABLE A-continued

| Device | Address | Label |
| --- | --- | --- |
| RAM 23 | 0800-08FF | |

A MEMR control line 32 becomes active to operate the memory select circuit 30 and an IORQ control line 33 becomes active to operate the I/O port select circuit 29. Thus, although the I/O ports occupy the same address space as the ROM 22, the ROM 22 is enabled only during memory read instructions and the I/O ports are enabled only during I/O instructions.

Commercially available devices are used throughout the system and for a detailed description of each device, reference is made to Appendix A.

Figure 2A:
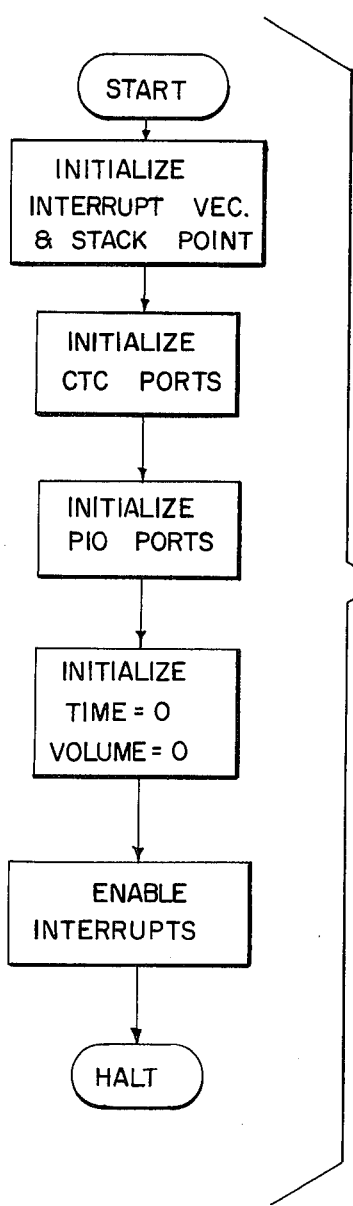
FIGS. 2A-2D are flow charts of the programs executed by the microprocessor which forms part of the air sampling system of FIG. 1.

The microprocessor system is primarily interrupt driven. Referring to FIG. 2A, when a power-on reset switch is activated the system is vectored to an initialization routine. Other interrupt vectors, a stack pointer, CTC ports and PIO ports are then initialized and the elapsed time and air volume numbers are set to zero. The maskable interrupts are then enabled and the system halts to await the occurrence of an interrupt.

Figure 2D:
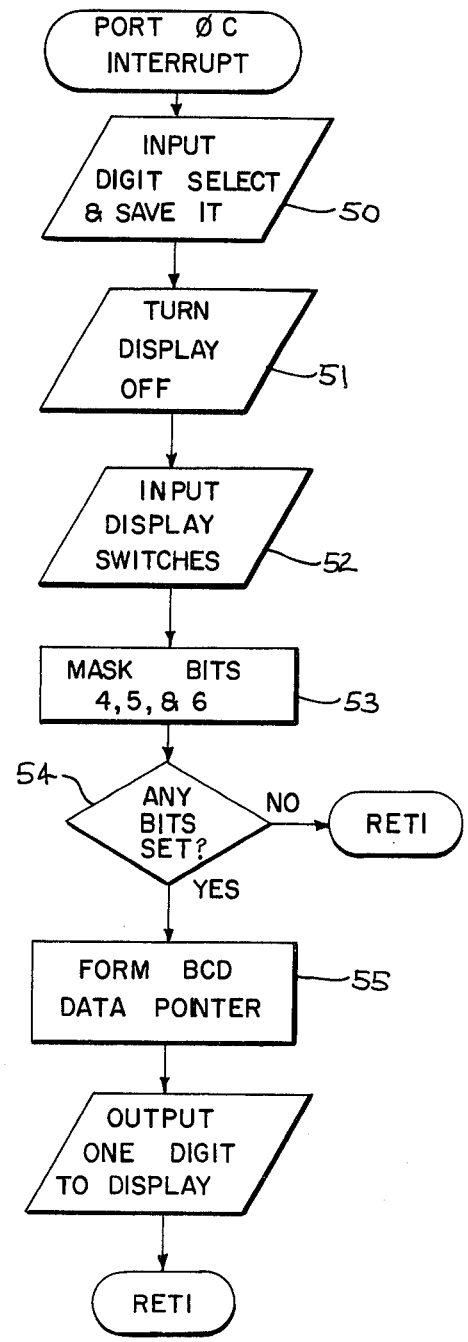
Figure 2B:
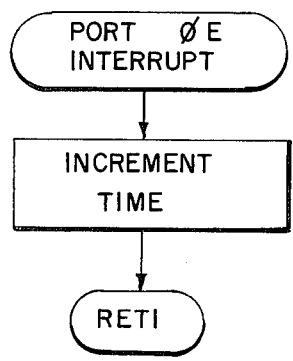

The CTC 31 is initialized to provide three real time clocks. The first clock generates an interrupt every one millisecond, the second generates an interrupt every 100 milliseconds and the third generates an interrupt every six seconds. As shown in FIG. 2B, when the six second clock generates an interrupt the system executes a set of instructions which updates the elapsed time by adding six seconds to the total. The system then returns to the background program which, as indicated above, is in the halt condition.

Figure 2C:
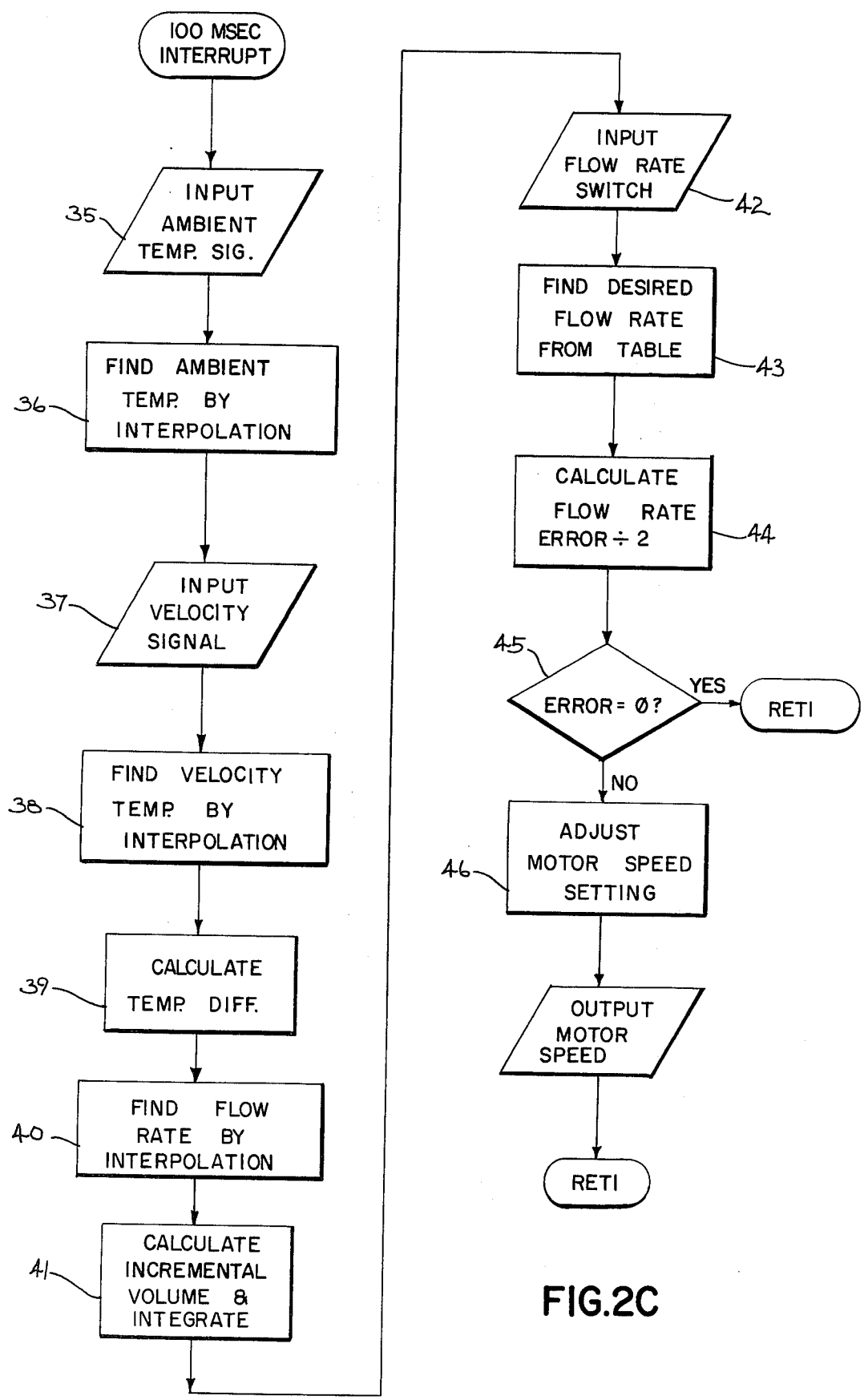

As shown in FIG. 2C, when the 100 millisecond clock interrupts the system the incremental volume of air passing through the housing 1 during the current 100 millisecond iteration is calculated and added to the total air volume number. More specifically, the ambient air temperature signal is first input through the A/D converter 16 as indicated at block 35 and the air temperature is calculated using a look-up table and an interpolation routine as indicated by process block 36. The air velocity signal from the thermal anemometer is then input as indicated at block 37 and an equivalent temperature is calculated using the same look-up table and interpolation routine as indicated at process block 38. The difference between the ambient temperature and the thermal anemometer equivalent temperature is indicative of the cooling effect of the air flow through the filter 5, and this difference is calculated next at process block 39. Air velocity, or flow rate, is then calculated from this temperature difference using a look-up table and an interpolation routine as indicated at process block 40. An incremental air flow volume is then calculated at process block 41 by multiplying this air velocity number times the cross sectional area of the passageway and by the 100 millisecond time increment. The resulting incremental air flow volume is added to the total air flow number for display to the user when requested. Any fluctuations in air flow through the filter 5 occur over very long time periods as compared to the 100 millisecond time increment employed in the preferred embodiment. As a result, the accumulation of incremental air flow volumes is a highly accurate measurement of the actual total air flow over any given time period.

As indicated at block 42, the 4-bit flow rate switch data is input next during each 100 millisecond interrupt through the PIO 26. The preselected flow rate is then calculated using a look-up table as indicated at process block 43. The preselected flow rate is then compared with the actual flow rate number as determined by the thermal anemometer, and a flow rate error is calculated as indicated at process block 44. If there is no significant error in the flow rate, as determined at decision block 45, the system returns from the interrupt to the halt state. Otherwise, a motor speed command is calculated at process block 46 and the command is output through the D/A converter 10 to change the air pump speed. The thermal anemometer is thus used as a feedback device to provide closed loop control of the air pump 6. This control loop is closed every 100 milliseconds to provide virtually continuous air flow control.

The one millisecond real time clock generates an interrupt which vectors the system to a display driver routine. Referring to FIG. 2D, this routine first executes an instruction indicated by block 50 to input the status of bits 0–3 of the PIO A port which indicate the last display digit to be updated. The display digits are then turned off as indicated by block 51 and the status of the data input switches 24 is input as indicated by block 52. All but bits 4, 5 and 6 are masked off as indicated by process block 53 and a test is made at decision block 54 to determine if any one of the three display push buttons has been depressed. If no display is requested, the routine returns to the background program. Otherwise, a pointer to the appropriate data (air flow rate, total elapsed time or total air volume) is formed as indicated by process block 55. One digit of the four-digit BCD number is output to the display 25 during each 1 millisecond interrupt and all four digits are thus output in sequence during each 4 millisecond time interval. As a result, the display 25 provides a visual indication of one of three selected numbers when the appropriate push button switch 24 is depressed.

A complete assembly language listing of the above described programs is provided in Appendix B. In addition, reference is made to an article in the February 1978 issue of *Computer Design* by Thomas A. Seim entitled "Numerical Interpolation For Microprocessor-Based Systems" for a detailed description of the interpolation subroutine used in the present invention.

It should be apparent to those skilled in the art that both the circuitry and the programs employed in the preferred embodiment can be varied considerably without departing from the spirit of the invention. Indeed, it is contemplated that a single, non-programmable large scale integrated circuit may be employed in a mass-produced implementation of the present invention.

Figure 3:
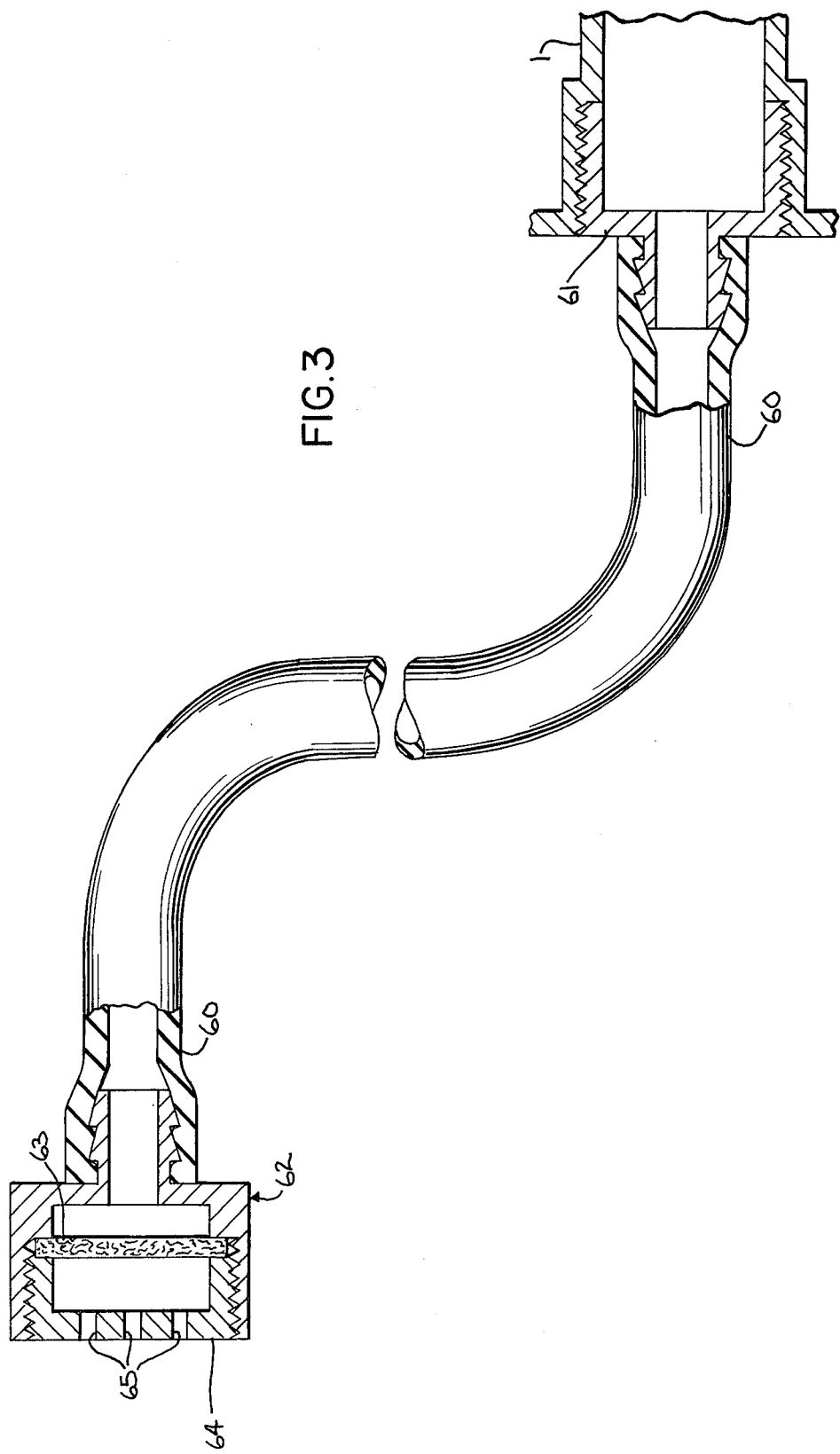
FIG. 3 is a partial view with parts cut away of an alternative embodiment of the housing and air passageway.

Also, the construction of the housing and the manner in which the air contaminant collection device is connected to receive air flowing through the air passageway can be varied considerably from that shown in the first preferred embodiment. Referring particularly to FIG. 3 for example, the housing 1 may be connected to a flexible tube 60 by a connector 61 which is received at the air intake end of the housing 1. The housing 1 may be attached to the user's belt, or placed in a pocket, and the tube 60 extends upward to a filter holder 62 which attaches to the user's shirt lapel. The filter holder 62 contains a disc-shaped air contaminant collection device 63 which is held in place by a cover 64, and sample air flows into air intake openings 65 formed in the cover 64. The air passageway through which sample air is pumped is thus physically extended by the tube 60 to allow the air intake to be positioned near the user's head while enabling the bulk of the apparatus to be conveniently and comfortably carried. There are numerous other types of air contaminant collection devices which may be employed in lieu of those shown and described herein and the invention is not limited by the type or construction of the air contaminant collection device which is used.

APPENDIX A

| Component | Description |
|---|---|
| Thermal anemometer 7 | No. 37A3 manufactured by Victor Engineering Corporation |
| Temperature sensor 12 | No. FN1A3 manufactured by Victor Engineering Corporation |
| Operational amplifiers 9, 11 and 13 | LM324 manufactured by National Semiconductor |
| Operational amplifier 8 | 7S9T2C manufactured by Fairchild Camera & Instrument Corp. |
| Analog Multiplexer 14 | MC14053B manufactured by Motorola, Inc. |
| Analog to Digital Converter 16 | ADC 804 manufactured by National Semiconductor |
| Digital to Analog Converter 10 | DAC 1002 manufactured by National Semiconductor |
| Microprocessor 20 | Z-80 8-bit microprocessor manufactured by Zilog, Inc. |
| Read-only memory 22 | 2K by 8 UVPROM number 2716 manufactured by Intel Corporation |
| RAM 23 | 256 by 8 static RAM number 3539 manufactured by Fairchild Camera & Instrument Corporation |
| CTC 31 | Z-80 counter timer circuit manufactured by Zilog, Inc. |
| PIO 26 | Z-80 parallel input output circuit manufactured by Zilog, Inc. |
| I/O port select 29 | SN74LS138 manufactured by Texas Instruments, Inc. |
| Memory Select 30 | SN74LS138 manufactured by Texas Instruments, Inc. |
| Segment Decoder Driver 28 | 9368PC manufactured by Fairchild Camera & Instrument Corporation |
| Digit Driver 27 | ULN-2804 manufactured by Sprague, Inc. |
| Display 25 | MAN 3640 manufactured by General Instruments, Inc. |

APPENDIX B

Air Sampler Device

Analog signals from two temperature sensitive transducers are input to the Z-80 microprocessor by means of a multiplexed analog to digital converter. One transducer is sensitive to air speed and thus forms a thermal anemometer. Interpolation of data stored in a table provides a corrected and accurate value for the air flow rate.

The air flow occurs through a duct of known cross-sectional area and thus the volume of air which flows through the duct is found by digitally integrating the air flow rate with respect to time.

A difference in flow rate from the desired flow rate is used to adjust the speed of the motor which drives the air pump.

By means of push-to-display switches, the following will be displayed on a four digit, seven-segment display:

(1) The actual air flow rate
(2) The elapsed time (duration of the sampling period)
(3) The volume (Air volume which has passed through the duct during the sampling period.)

I/O PORT NUMBERS

| | | | |
|---|---|---|---|
| ADCPT: | EQU | 00H | ; address of A to D converter |
| DACPT1: | EQU | 04H | ; address of D to A lower byte |
| DACPT2: | EQU | 05H | ; address of D to A bits 8 and 9 |
| DACXFR: | EQU | 08H | ; address of D to A data XFER command |
| CTCPT1: | EQU | 0CH | ; address of CTC # 1 timer/counter |
| CTCPT2: | EQU | 0DH | ; address of CTC # 2 timer/counter |
| CTCPT3: | EQU | 0EH | ; address of CTC # 3 timer/counter |

APPENDIX B-continued

| | | | |
|---|---|---|---|
| CTCPT4: | EQU | 0FH | ; address of CTC # 4 timer/counter |
| DSPPT: | EQU | 10H | ; address of PIO port A data |
| DSPCMD: | EQU | 11H | ; address of PIO port A command |
| SWTPT: | EQU | 12H | ; address of PIO port B data |
| SWTCMD: | EQU | 13H | ; address of PIO port B command |

2.00 M Hz Clock Frequency

I/O PORT DEFINITION

CTCPT1 -
    Timer mode of operation
    Interrupt enabled
    Divide by 16 pre-scaler
    Divide by 125 down counter
    One pulse out every 1 millisecond CTCPT2 -
    Counter mode of operation
    Interrupt enabled
    Divide by 100 down counter
    One pulse out every 100 milliseconds CTCPT3 -
    Counter mode of operation
    Interrupt enabled
    Divide by 60 down counter
    One pulse out every 6 seconds (0.1 minute)

CTCPT4 -
    Unused
    No interrupt allowed

DSPPT -
    Control mode of operation
    No interrupt allowed
    Bit 7 through 0 are outputs
    Bit 7 - BCD bit 3
    Bit 6 - BCD bit 2
    Bit 5 - BCD bit 1
    Bit 4 - BCD bit 0
    Bit 3 - Digit 3 select line
    Bit 2 - Digit 2 select line
    Bit 1 - Digit 1 select line
    Bit 0 - Digit 0 select line SWTPT -
    Control mode of operation
    No interrupt allowed
    Bit 7 is output
    Bit 6 through 0 are inputs
    Bit 7 - Multiplex channel select   L = REFerence signal
                                                        H = VELocity signal
    Bit 6 - Volume switch
    Bit 5 - Elapsed Time switch
    Bit 4 - Flow Rate switch
    Bit 3 - Bit 3 of Flow Rate select switch
    Bit 2 - Bit 2 of Flow Rate select switch
    Bit 1 - Bit 1 of Flow Rate select switch
    Bit 0 - Bit 0 of Flow Rate select switch

RAM ALLOCATION

| | | | |
|---|---|---|---|
| RAM: | EQU | 0800H | ; lowest RAM address |
| STACK: | EQU | 08FFH | ; highest RAM address |
| BCDTIME: | EQU | RAM | ; 2 bytes - BCD Elapsed Time |
| BCDVOL: | EQU | RAM+2 | ; 2 bytes - BCD Volume |
| BCDRATE: | EQU | RAM+4 | ; 2 bytes - BCD Flow Rate |
| BNVOL: | EQU | RAM+6 | ; 6 bytes - binary Volume |
| BNRATE: | EQU | RAM+0CH | ; 2 bytes - binary Flow Rate |
| BNREF: | EQU | RAM+0EH | ; 2 bytes - binary Reference Temperature |
| DIGIT: | EQU | RAM+10H | ; 1 byte - digit select signals |
| MOTOR: | EQU | RAM+11H | ; 1 byte - motor speed setting |
| SHFVOL: | EQU | RAM+12H | ; 4 bytes - right shifted Volume |

;
CONSTANT DEFINITION
;
| | | | |
|---|---|---|---|
| VECTBS: | EQU | 07F0H | ; 16 bytes - location of interrupt table in ROM |
| VECT: | EQU | VECTBS/256 | ; interrupt pointer (high byte) |
| CTCVECT: | EQU | VECTBS−VECT*256 | ; CTC interrupt pointer (low byte) |
| PIOVECT: | EQU | CTCVECT+08H | ; PIO interrupt pointer (low byte) |
| CTCMD1: | EQU | 85H | |
| CTCMD2: | EQU | 0C5H | |
| PIOMD3: | EQU | 0CFH | |
| TIME 1: | EQU | 125 | |
| TIME 2: | EQU | 100 | |
| TIME 3: | EQU | 60 | |
| DSPBITS: | EQU | 00H | |
| DSPINT: | EQU | 07H | |
| SWTBITS: | EQU | 7FH | |
| SWTINT: | EQU | 07H | |

;
;
;
PROGRAM
;
; Initialize CPU registers
```
START:      LD      SP,STACK
            LD      A,VECT
            LD      I,A
;
; Initialize CTCPT1
            LD      A,CTCMD1
            OUT     CTCPT1,A
            LD      A,TIME1
            OUT     CTCPT1,A
;
;Initialize CTCPT2
            LD      A,CTCMD2
            OUT     CTCPT2,A
            LD      A,TIME2
            OUT     CTCPT2,A
;
; Initialize CTCPT3
            LD      A,CTCMD2
            OUT     CTCPT3,A
            LD      A,TIME3
            OUT     CTCPT3,A
;
; Load CTC interrupt vector
            LD      A,CTCVECT
            OUT     CTCPT1,A
;
; Initialize PIO DSPPT
            LD      A,PIOMD3
            OUT     DSPCMD,A
            LD      A,DSPBITS
            OUT     DSPCMD,A
            LD      A,DSPINT
            OUT     DSPCMD,A
;
; Initialize PIO SWTPT
            LD      A,PIOMD3
            OUT     SWTCMD,A
            LD      A,SWTBITS
            OUT     SWTCMD,A
            LD      A,SWTINT
            OUT     SWTCMD,A
;
; Initialize RAM
            LD      HL, 0000H
            LD      (BNVOL),HL
            LD      (BNVOL+2),HL
            LD      (BCDTIME),HL
;
; Enable interrupts and wait
WAIT:       EI
            HALT
            JR      WAIT
;
;
; Increment time by 0.1 minute (1 LSB)
TIME:       DI
            LD      A,(BCDTIME)
            ADD     01H
```

APPENDIX B-continued

| | | | |
|---|---|---|---|
| | DAA | | ; add 1 to lower BCD numbers |
| | LD | (BCDTIME),A | |
| | JR | NC,TIMERTN | ; jump, if no carry was generated |
| ; | | | |
| | LD | A,(BCDTIME+1) | |
| | ADD | 01H | |
| | DAA | | ; add 1 to upper BCD numbers |
| | LD | (BCDTIME+1),A | |
| ; | | | |
| TIMERTN: | RETI | | |
| ; | | | |
| ; | | | |
| ; Multiplex LED digital display | | | |
| DISPLAY: | DI | | |
| | IN | A,(DSPPT) | |
| | LD | (DIGIT),A | ; save digit select signals |
| | LD | A,00H | |
| | OUT | DSPPT,A | ; blank the display |
| | IN | A,(SWTPT) | |
| | AND | 70H | ; mask bits 4, 5 & 6 |
| | JR | NZ,POINT | ; jump if any bit is set |
| | RETI | | |
| ; Form pointer - BCD data to be displayed | | | |
| POINT: | LD | HL,BCDTIME | |
| | BIT | 5,A | |
| | JR | NZ,SHIFT | ; jump if TIME switch is ON |
| | LD | HL,BCDVOL | |
| | BIT | 6,A | |
| | JR | NZ,SHIFT | ; jump if VOLUME switch is ON |
| | LD | HL,BCDRATE | ; RATE switch is ON |
| ; | | | |
| ; Shift selected digital signal | | | |
| SHIFT: | LD | A,(DIGIT) | |
| | AND | 0FH | ; mask bits 3, 2, 1 & 0 |
| | JR | Z,SET0 | ; jump if no digit is selected |
| | BIT | 3,A | |
| | JR | NZ,SET0 | ; jump if bit 3 = 1 |
| | BIT | 0,A | |
| | JR | NZ,SET1 | ; jump if bit 0 = 1 |
| ; | | | |
| | INC | HL | ; increment pointer to upper BCD digits |
| | BIT | 1,A | |
| | JR | NZ,SET2 | ; jump if bit 1 = 1 |
| | JR | SET3 | ; bit 2 = 1 |
| ; | | | |
| ; bit 3 = 1 | | | |
| ; | | | |
| SET0: | RRD | | ; get digit |
| | LD | B,A | ; save digit in B |
| | RLD | | ; restore memory |
| | LD | A,B | ; retrieve digit |
| | SLA | A | |
| | SLA | A | |
| | SLA | A | |
| | SLA | A | ; shift digit 4 bits left |
| | OUT | DSPPT,A | ; move BCD data to display |
| | SET | 0,A | ; select digit 0 |
| | OUT | DSPPT,A | ; move digit select to display |
| | RETI | | |
| ; | | | |
| SET1: | RLD | | ; get digit |
| | LD | B,A | ; save digit in B |
| | RRD | | ; restore memory |
| | LD | A,B | ; retrieve digit |
| | SLA | A | |
| | SLA | A | |
| | SLA | A | |
| | SLA | A | ; shift digit 4 bits left |

APPENDIX B-continued

| | | | |
|---|---|---|---|
| | OUT | DSPPT,A | ; move BCD digit to display |
| | SET | 1,A | ; select digit 1 |
| | OUT | DSPPT,A | ; move digit select to display |
| | RETI | | |
| ; | | | |
| ; | | | |
| SET2: | RLD | | ; get digit |
| | LD | B,A | ; save digit in B |
| | RLD | | ; restore memory |
| | LD | A,B | ; retrieve digit |
| | SLA | A | |
| | SLA | A | |
| | SLA | A | |
| | SLA | A | ; shift digit 4 bits left |
| | OUT | DSPPT,A | ; move BCD digit to display |
| | SET | 2,A | ; select digit 2 |
| | OUT | DSPPT,A | ; move digit select to display |
| | RETI | | |
| ; | | | |
| SET3: | RLD | | ; get digit |
| | LD | B,A | ; save digit in B |
| | RRD | | ; restore memory |
| | LD | A,B | ; retrieve digit |
| | SLA | A | |
| | SLA | A | |
| | SLA | A | |
| | SLA | A | ; shift digit 4 bits left |
| | OUT | DSPPT,A | ; move BCD digit to display |
| | SET | 3,A | ; select digit three |
| | OUT | DSPPT,A | ; move digit select to display |
| | RETI | | |
| ; | | | |
| ; Calculate air Flow Rate and Volume | | | |
| ; | | | |
| ; Convert Reference Temperature to a binary value | | | |
| COMPUTE: | DI | | |
| | IN | A,(SWTPT) | |
| | RES | 7,A | ; select Reference channel of multiplexer |
| | OUT | SWTPT,A | |
| | OUT | ADCPT,A | ; write anything to start A to D conversion |
| ; Allow 100 usec for conversion | | | |
| | LD | B,18 | |
| LOOP1: | DJNZ | LOOP1 | ; wait |
| | IN | A,(ADCPT) | ; get 8 bit value |
| | LD | L,A | |
| | LD | H,00 | ; move data to HL |
| | LD | DE,REFTBL | ; load DE with address of interpolation table |
| | CALL | INTERP | |
| | LD | (BNREF),HL | ; save Reference Temperature |
| ; | | | |
| ; Convert Flow Rate signal to binary value | | | |
| | IN | A,(SWTPT) | |
| | SET | 7,A | ; select Velocity channel of multiplexer |
| | OUT | SWTPT,A | |
| | OUT | ADCPT,A | ; write anything to start A to O conversion |
| ; Allow 100 usec for conversion | | | |
| | LD | B,18 | |
| LOOP2: | DJNZ | LOOP2 | ; wait |
| | IN | A,(ADCPT) | ; get 8 bit value |
| | LD | L,A | |
| | LD | H,00 | ; move data to HL |
| | LD | DE,VELTBL | ; load DE with |

APPENDIX B-continued

```
                CALL    INTERP          ; address of
                                        ; interpolation table
; Find Temperature difference
                LD      DE,(BNREF)
                XOR     A               ; clear carry bit
                SBC     HL,DE           ; DIFF = HL − DE
;
; Find air Flow Rate
; Interpolation table contains data consistent with specific
; temperature transducers which are used, the cross-sectional
; area of the duct, and non-uniform but predictable air
; flow across the area of the duct
;
; Flow Rate is given in Cubic Feet per Minute × 2**12
;               0. 003531 CFM = 14
;               0. 106 CFM = 434
; (Fractions are not allowed for binary arithmetic)
                LD      DE,RATETBL      ; load DE with
                                        ; address of
                                        ; interpolation table
                CALL    INTERP
                LD      (BNRATE),HL     ; save Flow Rate
; Convert to BCD value
                LD      DE,BCDRATE      ; load DE with
                                        ; pointer for
                                        ; BCD results
                CALL    BCD
;
;
; Integrate air Volume
; Volume = Volume + Flow Rate × Sampling Period
; Sampling Period is given in Minutes × 2**17
;               0. 1 second = 0. 00166 minute = 218
; (Fractions are not allowed for binary arithmetic)
                LD      HL,(BNRATE)
                LD      DE,218
                CALL    MULT            ; 32 bit result
                CALL    ADD48           ; add 32 bit incremen-
                                        ; tal volume to 48 bit
                                        ; total volume
                CALL    RS29            ; right shift Volume
                                        ; 29 bits for BCD
                                        ; conversion
                CALL    DIV100          ; divide Volume by
                                        ; 100
                LD      HL,(SHFVOL+2)   ; load HL with binary
                                        ; Volume
                LD      DE,BCDVOL       ; load DE with
                                        ; pointer for
                                        ; BCD results
                CALL    BCD
;
;
; Adjust motor speed
                IN      A,(SWTPT)
                AND     0FH             ; mask bits 3, 2, 1 & 0
                LD      L,A
                LD      H,00H           ; move switch setting
                                        ; to HL
                LD      DE,SWTTBL       ; load DE with
                                        ; address of
                                        ; table of Flow
                                        ; Rate switch settings
                ADD     HL,DE
                LD      A,(BNRATE)      ; form table pointer
                LD      B,A             ; load B with actual
                                        ; Flow Rate
                LD      A,(HL)          ; load A with desired
                                        ; Flow Rate
                SUB     B               ; A = Flow Rate
                                        ; Error
                SRA     A               ; divide Error by 2
                JR      Z,COMPRET       ; jump if zero LD      B,A             ; move Error to B
                LD      A,(MOTOR)       ; load motor setting
                                        ; into A
                ADD     B               ; adjust motor setting
                LD      (MOTOR),A       ; save motor setting OUT     DACPT2,A        ; output upper 2 bits
                SLA     A
                SLA     A               ; position lower 6 bits
                                        ; to be loaded into
                                        ; lower byte of DAC
                OUT     DACPT1,A
                OUT     DACXFR,A        ; write anything to
                                        ; transfer 10 bits to
                                        ; DAC's output latches
COMPRET:        RETI
;
; MULT subroutine multiplies DE by HL and stores the
; results in DEHL
MULT:           NOP
                RET
;
; BCD subroutine converts a 2 byte binary number to a 4
; digit BCD number
BCD:            NOP
                RET
;
; INTERP subroutine performs second order interpolation
; on a sixteen bit number. See additional documentation
; for program listing, flow chart and explanation.
INTERP:         NOP
                RET
;
; ADD48 subroutine adds a 32 bit number in DEHL to a 48 bit
; number stored in six consecutive memory location beginning
; at BNVOL.
ADD48:          NOP
                RET
;
; RS29 subroutine takes the 48 bit number stored at BNVOL,
; shifts it 29 bits and stores the result in four memory
; locations beginning at SHFVOL.
RS29:           NOP
                RET
;
; DIV100 subroutine divides the number in SHFVOL by 100
; and stores the result in 2 bytes of RAM starting at
; SHFVOL+2.
DIV100:         NOP
                RET
;
;
; Table for interpolation of Reference Temperature
; Arbitrary data is shown
REFTBL:         DW      0000, 0001, 0002, 0004
;
;
; Table for interpolation of Velocity Temperature
; Arbitrary data is shown
VELTBL:         DW      0000, 0002, 0008, 0016
;
; Table for interpolation of Flow Rate
; Arbitrary data is shown
RATETBL:        DW      0000, 0004, 0007, 0009
;
;
; Table of switch selectable Air Flow Rates
; One of sixteen Rates is possible
; Arbitrary data is shown
SWTTBL:         DB      01, 02, 04, 08, 16, 32, 64, 128, 255
;
;
; Interrupt Table
                ORG     VECTBS
                DW      DISPLAY, COMPUTE, TIME, START
                DW      START, START, START, START
;
;
                END     START
```

APPENDIX B-continued

INTERPOLATION SUBROUTINE

```
interp:  push  de              ; save table base address
         ld    (ram+x),hl      ; save data
; the abcissa spacing is a power of 2
; the interval which x falls in can be found by
; dividing x by the abcissa spacing.
         ld    b,(ix+hexp)     ; use msb's as index
         ld    de,0
         call  ars32
; index is multiplied by 2 for addressing a
; double precision table
         add   hl,hl            ; hl = hl*2
         pop   de
; table pointer = table base address + index
         add   hl,de
; find f(0) and f(1)
         ld    e,(hl)          ; get f(0) − 2 consecutive bytes
         inc   hl              ; de register pair = f(0)
         ld    d,(hl)
         inc   hl
         ld    c,(hl)          ; get f(1)
         inc   hl              ; bc register pair = f(1)
         ld    b,(hl)
         inc   hl
; save table pointer
         push  hl
         ex    de,hl
; output result is initialized to the first term of formula
         ld    (ram+fx),hl     ; initialize result=f(0)
; compute first differences (d10 and d11)
         ex    de,hl           ; de = f(0)
         ld    l,c             ; hl = f(1)
         xor   a
         ld    h,b
         sbc   hl,de           ; f(1) − f(0)
         ld    (ram+d10),hl    ; save 1st difference
; unstack table pointer
         pop   hl
         ld    e,c
         ld    d,b             ; de = f(1)
         ld    c,(hl)          ; hl = f(2)
         inc   hl
         ld    h,(hl)
         xor   a
         ld    l,c
         sbc   hl,de           ;hl=f(2) − f(1)
         ld    (ram+d11),hl    ; save 1st difference
; compute second difference (d11 − d10)
         ex    de,hl
         ld    hl,(ram+d10)
         ex    de,hl           ; hl = d11
         xor   a
         sbc   hl,de           ; d11 − d10
         ld    (ram+d120),hl   ; save 2nd difference
; compute second term of formula - (x−x(0)*d10/(2**hexp)
         ld    hl,(ram+x)      ; get x
         ld    a,l             ; x−x(0) is calculated by stripping the
         and   (ix+mask)       ; most sig bits (valid be-
                                 cause the
         ld    e,a             ; abcissa spacing is a power of 2)
         ld    d,0             ; de = (x−x(0))
         ld    hl,(ram+d10)
         call  mult            ; (x−x(0))*d10
; division by h is done with right shift
         ld    b,(ix+hexp)
         call  ars32           ; hl=(x−x(0))*d10/(2**hexp)
; fx = fx + second term
         ex    de,hl
         ld    hl,(ram+fx)
         add   hl,de           ; accumulate terms
         ld    (ram+fx),hl
; compute third term of formula
         ld    de,(ram+x)      ; load data point
         ld    d,0ffh
         ld    a,(ix+mask)
         cpl
         or    e
         ld    e,a             ; de = x − x(1)
         ld    hl,(ram+x)
         ld    a,l
         and   (ix+mask)
         ld    l,a
```

APPENDIX B-continued

```
         ld    h,0             ; hl = (x−x(0))
         call  mult            ; hl = (x−x(0)*(x−x(1))
         ld    de,(ram+d120)
         call  mult            ; hl = (x−x(1))*(x−x(0))*d120
         ld    b,(ix+hexp)
         sla   b
         inc   b               ; b=hexp*2+1
         call  ars32           ; hl = hl/(2*h**2)
         ld    de,(ram+fx)     ; accumulate last term
         add   hl,de
         ret
; this routine will shift a four byte number to the right
; on entrance
;        dehl contains the number
;        b contains the number of shift operations to be
; performed on exit
;        dehl contains the shifted number
ars32:   sra   d
         rr    e
         rr    h
         rr    l
         djnz  ars32           ; repeat if more shifts are to be done
         ret
; sixteen bit integer multiply
;        on entrance: multiplier in hl
;                     multiplicand in de
;        on exit: result in dehl
mult:    ld    b,32            ; number of bits
         ld    a,h
         ld    c,l             ; move multiplier to bc
         ex    de,hl           ; move multiplicand to hl
         ld    de,00           ; clear upper byte of
                                 multiplicand
         ld    (ram+add1),de
         ld    (ram+add2),de   ; clear partial result
         bit   7,h
         jr    z,mloop         ; jump if multiplicand is
                                 positive
         ld    de,0ffffh       ; make upper byte of
                               ; multiplicand negative
mloop:   sra   a
         rr    c               ; shift multiplier right
         ld    (ram+mult1),de
         ld    (ram+mult2),hl  ; save multiplicand
         jr    nc,noadd
         call  add32
         ld    (ram+add1),hl
         ld    (ram+add2),de   ; save partial result
noadd:   ld    de,(ram+mult1)
         ld    hl,(ram+mult2)  ; recall multiplicand
         call  als32           ; shift multiplier left
         djnz  mloop
         ld    hl,(ram+add1)
         ld    de,(ram+add2)   ; put result in dehl
         ret
; this routine will shift a four byte number to the left one
; bit.
; dehl = dehl*2
als32:   add   hl,hl
         ex    de,hl
         adc   hl,hl
         ex    de,hl
         ret
; this routine adds two four byte numbers
; on entrance  dehl contains one number
;              add2 and add1 contain the other number
; on exit      dehl contains the sum
add32:   push  bc              ; save bc
         ld    bc,(ram+add1)   ; retrieve lower two bytes
         add   hl,bc
         ex    de,hl           ; position upper two bytes
         ld    bc,(ram+add2)   ; retrieve upper two bytes
         adc   hl,bc
         ex    de,hl           ; reposition bytes
         pop   bc
         ret
```

I claim:

1. A personal air sampling device which comprises:
a housing defining an air passageway having an air intake and an exhaust;

an air pump mounted to the housing for pumping air through the air passageway;

an air contaminant collection device connected to collect material in the air flowing through the air passageway;

air velocity sensor means mounted to the housing and being operable to generate a signal indicative of the velocity of the air passing through the air passageway;

converter means coupled to the velocity sensor means for periodically reading the velocity sensor signal and converting it to a digital velocity number indicative of the velocity of the air passing through the air passageway;

first calculation means coupled to the converter means for receiving said digital velocity number and calculating an incremental air flow volume number which is indicative of the volume of air flowing through the air passageway during a preset time increment;

second calculation means coupled to the first calculation means for adding together each calculated incremental air flow volume number to form a total air volume number; and display means coupled to the second calculation means to receive the total air volume number and provide a visual indication of that number.

2. The personal air sampling device as recited in claim 1 in which said air velocity sensor is a thermal anemometer.

3. The personal air sampling device as recited in claim 2 in which said converter means includes an analog to digital converter circuit which converts the thermal anenometer signal to digital form and linearizing means for converting the digitized thermal anemometer signal to a corresponding digital velocity number.

4. The personal air sampling device as recited in claim 3 in which said linearizing means employs a stored look-up table for converting the digitized thermal anemometer signal to the corresponding digital velocity number.

5. The personal air sampling device as recited in claim 1 in which said first calculation means includes multiplier means for multiplying the digital velocity number times a digital constant number which represents the effective cross-sectional area of the air passageway.

6. The personal air sampling device as recited in claim 5 in which said multiplier means also multiplies said digital velocity number by a digital time increment number which represents the time period between each of said periodic readings of the velocity signal by said converter means.

7. A personal air sampling device which comprises:
a housing which defines an air passageway through which sampled air flows;
an air contaminant collection device connected to the air passageway to collect material in the sampled air;
an air pump mounted to the housing for pumping sample air through the air passageway;
a thermal anemometer disposed in the air passageway and operable to generate an analog electrical signal indicative of the velocity of the sample air flowing through the air passageway;

an analog to digital converter circuit connected to receive the analog signal generated by the thermal anemometer and convert it to a digital number indicative of sample air velocity;

digital processor means coupled to said analog to digital converter circuit and being operable to periodically read the digital air velocity number generated by said analog to digital converter and calculate a total air volume number therefrom which indicates the total sample air flowing through the air passageway during a sample period; and a display coupled to the digital processor means for providing a visual indication of the total air volume number.

8. The personal air sampling device as recited in claim 7 in which the digital processor means is coupled to said air pump by a digital to analog circuit and the processor is operable in response to the digital velocity number from the analog to digital converter circuit to control the speed of the air pumps and to thereby maintain the air velocity in the air passageway at a selected level.

9. The personal air sampling device as recited in claim 7 in which said digital processor means is a microprocessor system and the calculations are performed in accordance with instructions stored in a memory.

10. The personal air sampling device as recited in claim 7 in which said digital processor means also calculates a total sample period number and said display is operable to provide a visual indication of the total sample period number.

11. A personal air sampling device which comprises:
a housing defining an air passageway having an air intake and an exhaust;
an air pump mounted to the housing for pumping sampled air through the air passageway;
a tube connected to the housing to transport sampled air to the air intake of said air passageway;
an air contaminant collection device connected to the tube and positioned to collect material in the sampled air transported by the tube;
air velocity sensor means mounted to the housing and being operable to generate a signal indicative of the velocity of the air passing through the air passageway;
converter means coupled to the velocity sensor means for periodically reading the velocity sensor signal and converting it to a digital velocity number indicative of the velocity of the air passing through the air passageway;
first calculation means coupled to the converter means for receiving said digital velocity number and calculating an incremental air flow volume number which is indicative of the volume of air flowing through the air passageway during a preset time increment;
second calculation means coupled to the first calculation means for adding together each calculated incremental air flow volume number to form a total air volume number; and
display means coupled to the second calculation means to receive the total air volume number and provide a visual indication of that number.

* * * * *